US009120730B2

(12) United States Patent
Shinohara et al.

(10) Patent No.: US 9,120,730 B2
(45) Date of Patent: Sep. 1, 2015

(54) SURFACE MODIFIED MATERIAL, SULFONIMIDE COMPOUND FOR SURFACE MODIFICATION, AND FUEL CELL

(75) Inventors: Akihiro Shinohara, Nagakute (JP); Naoki Hasegawa, Nagakute (JP)

(73) Assignee: KABUSHIKI KAISHA TOYOTA CHUO KENKYUSHO, Nagakute-shi (JP)

( * ) Notice: Subject to any disclaimer, the term of this patent is extended or adjusted under 35 U.S.C. 154(b) by 0 days.

(21) Appl. No.: 13/415,396

(22) Filed: Mar. 8, 2012

(65) Prior Publication Data

US 2012/0253070 A1    Oct. 4, 2012

(30) Foreign Application Priority Data

Mar. 30, 2011  (JP) .................. 2011-074632

(51) Int. Cl.
| | | |
|---|---|---|
| *B01J 31/02* | (2006.01) | |
| *C07C 311/48* | (2006.01) | |
| *H01M 8/10* | (2006.01) | |
| *H01M 4/90* | (2006.01) | |
| *H01M 4/86* | (2006.01) | |

(52) U.S. Cl.
CPC ........... *C07C 311/48* (2013.01); *B01J 31/0227* (2013.01); *H01M 4/8668* (2013.01); *H01M 4/9075* (2013.01); *H01M 8/103* (2013.01); *H01M 8/1032* (2013.01); *H01M 2008/1095* (2013.01); *Y02E 60/522* (2013.01)

(58) Field of Classification Search
USPC .......................... 529/242; 526/242
See application file for complete search history.

(56) References Cited

U.S. PATENT DOCUMENTS

| | | | | |
|---|---|---|---|---|
| 2003/0175523 | A1* | 9/2003 | Moya | 428/421 |
| 2004/0024123 | A1* | 2/2004 | Moya | 525/72 |
| 2006/0177717 | A1* | 8/2006 | Teasley et al. | 429/33 |
| 2007/0202373 | A1* | 8/2007 | Hojo et al. | 429/33 |

(Continued)

FOREIGN PATENT DOCUMENTS

| | | |
|---|---|---|
| JP | A-10-510797 | 10/1998 |
| JP | A-2005-187629 | 7/2005 |

(Continued)

OTHER PUBLICATIONS

Liu, "Synthesis and Modification of Mesoporous Carbons and their Application in Polymer Electrolyte Membrane Fuel Cells", A Dissertation Presented to the Graduate School of Clemson University, Dec. 2009.*

(Continued)

*Primary Examiner* — Patrick Ryan
*Assistant Examiner* — Lucas J O'Donnell
(74) *Attorney, Agent, or Firm* — Oliff PLC (57) ABSTRACT

There are provided a surface modified material comprising a base material, and one or more kinds of sulfonimide compound groups bonded onto the surface of the base material via one or more linking groups -A-Y'— (A is a direct bond or an organic group. Y' is a bonding site with the base material.); the sulfonimide compound group comprising, in its molecular structure, one or more linking groups -A-Y'— and two or more sulfonimide groups; as well as a fuel cell using the surface modified material for a catalyst layer. There is also provided a sulfonimide compound for surface modification comprising one or more reactive end groups -A-Y (A is a direct bond or an organic group. Y is a reactive functional group.) and two or more sulfonimide groups.

6 Claims, 3 Drawing Sheets

(56) References Cited

U.S. PATENT DOCUMENTS

2007/0265426 A1* 11/2007 Allcock et al. ................ 528/398
2009/0155662 A1* 6/2009 Durante et al. ................ 429/33

FOREIGN PATENT DOCUMENTS

| JP | A-2007-220370 | 8/2007 |
| JP | A-2009-226318 | 10/2009 |
| JP | A-2009-231049 | 10/2009 |
| JP | A-2009-295441 | 12/2009 |
| JP | A-2010-24263 | 2/2010 |

OTHER PUBLICATIONS

Creager, S., et al., "Electrochemical Grafting of an Aryl Fluorosulfonimide Electrolyte onto Glassy Carbon," Langmuir, 2006, vol. 22, pp. 10747-10753.

Mizuhata, H., et al., "Morphological control of PEMFC electrode by graft polymerization of polymer electrolyte onto platinum-supported carbon black," Journal of Power Sources, 2004, vol. 138, pp. 25-30.

Aug. 26, 2014 Office Action issued in Japanese Patent Application No. 2012-042527 w/translation.

* cited by examiner

SURFACE MODIFIED MATERIAL, SULFONIMIDE COMPOUND FOR SURFACE MODIFICATION, AND FUEL CELL

BACKGROUND OF THE INVENTION

1. Field of the Invention

The present invention relates to a surface modified material, a sulfonimide compound for surface modification, and a fuel cell, and more specifically, to a surface modified material prepared by bonding a sulfonimide compound onto a surface of a base material, a sulfonimide compound for surface modification for use in the production of such a surface modified material, and a fuel cell using such a surface modified material for a catalyst layer.

2. Description of the Related Art

Chemically bonding various kinds of organic compounds onto a surface of a base material allows imparting functions of the organic compounds and/or new functions to the base material. Moreover, in such a material prepared by chemically bonding an organic compound onto a surface of a base material (surface modified material), the organic compounds is unlikely to fall out, and therefore deterioration of imparted functions is characteristically low. A number of such surface modified materials and methods for producing the same have been heretofore suggested.

For example, Patent Document 1 discloses a carbon product obtained by adding a graphite powder and 4-chlorobenzene diazonium hexafluorophosphate to water, stirring the mixture for 20 minutes, filtering and drying the product.

The document describes that it is possible to obtain a graphite powder containing a chlorophenyl group without providing a current sufficient for reducing a diazonium salt from outside by such a method.

Patent Document 2 discloses a platinum-supported carbon prepared by having platinum particles supported on a surface modified carbon material with N,N-dimethyl amino phenyl group introduced onto its surface.

The document describes that modifying the surface of the carbon material with an organic group containing nitrogen atoms allows platinum fine particles to be highly dispersed on the surface of the carbon material and strongly supported onto the same.

Patent Document 3 discloses that a platinum-supported carbon prepared by having platinum particles supported on a surface modified carbon material with a nitrophenyl group, an anthraquinonyl group, or N-methyl phthalimide introduced onto its surface.

The document describes that modifying the surface of a carbon material with an organic group having a reducing potential on a high potential side higher than −2.5 V relative to SCE allows platinum fine particles to be highly dispersed on the surface of the carbon material and strongly supported onto the same.

Non-patent Document 1 discloses a material having benzene sulfonimide ($-C_6H_4-SO_2N^-SO_2CF_3$) electrochemically supported on the surface of carbon.

Patent Document 4 discloses a carbon catalyst having poly-p-sodium styrenesulfonate introduced onto a surface of a carbon material by grafting by allowing reaction between the carbon material in which its surface is covered with a silane coupling agent and p-sodium styrenesulfonate.

The document describes that the oxygen reduction activity of the carbon catalyst is improved by introducing ion-exchanging functional groups on the surface of the carbon catalyst.

Non-patent Document 2 discloses introduction of benzyl alcohol onto the surface of carbon, and a carbon material prepared by graft polymerization using the surface as a starting point. This document describes that such a carbon material can be utilized as a catalyst layer for fuel cells.

In addition, Patent Document 5 discloses polybutyl methacrylate-modified carbon black obtained by:

(1) synthesizing polymerization initiator-modified carbon black by introducing a polymerization initiator 2-bromoisobutyric acid-p-(bromomethyl)benzyl on the surface of carbon black, and (2) allowing polymerization by adding butyl methacrylate and 4,4'-dinonyl-2,2'-bipyridyl to a dispersion of the polymerization initiator-modified carbon black.

This document describes that introducing a functional group (polymerization initiating group) having polymerization initiating ability into a methyl halide aromatic compound or its derivative allows introduction of a polymerization initiating group on the surface of various base materials having a nucleophilic functional group, and allows grafting of polymer chains at a high density onto the surface of the base material using the polymerization initiating group as a starting point.

A catalyst layer of a solid polymer fuel cell generally consists of a complex of carbon which supports an electrode catalyst, such as platinum, and catalyst layer ionomers. The catalyst layer ionomers generally use a fluorinated electrolytic polymer such as Nafion (registered trademark) therein. In order to improve the performance of the fuel cell, the higher the oxygen permeation and proton conductivity of the catalyst layer ionomers, the better.

However, known catalyst layer ionomers have low oxygen permeation, and therefore have the problem that oxygen reduction efficiency of Pt is low and high performance cannot be obtained. Moreover, there has been the problem that lowering the equivalent weight (EW) of the catalyst layer ionomers in order to improve proton conductivity makes the catalyst layer ionomers flow out due to water more easily.

In order to solve these problems, chemically bonding an electrolyte on a surface of a carbon carrier, that is, modifying the surface of the carbon carrier with the electrolyte is also possible. Methods for having an organic compound supported onto the surface of carbon generally involves, as described in Patent Documents 1 to 3 and Non-patent Document 1, using a diazonium salt. It is considered that the surface of the carbon carrier can be modified with the electrolyte by introducing a benzene ring onto the surface of carbon using a diazonium salt and further introducing an acid group into the benzene ring.

However, heretofore, it has been possible only to introduce a single acid group, or two acid groups at the most for a single benzene ring. Moreover, introducing many benzene rings (acid groups) into a graphite plane increases resistance, thereby lowering electric conductivity of graphite and performance. In addition, since the graphite plane wants to maintain its $sp^2$ property, heat and/or potential scan cause benzene rings to leave the plane, and consequently cause acid groups to leave.

Meanwhile, grafting using no diazonium salt has also been reported (Patent Document 4, Non-patent Document 2). These techniques are thought to have low performance at a low humidity because the grafted material is a hydrocarbon material which has lower acidity than a fluorinated material does.

PRIOR ART DOCUMENTS

Patent Documents

[Patent Document 1] Japanese Translation of PCT International Application No. H10-510797
[Patent Document 2] Japanese Patent Application Laid-Open No. 2009-226318
[Patent Document 3] Japanese Patent Application Laid-Open No. 2009-231049
[Patent Document 4] Japanese Patent Application Laid-Open No. 2009-295441
[Patent Document 5] Japanese Patent Application Laid-Open No. 2010-024263

Non-Patent Documents

[Non-patent Document 1] DesMarteau, Langmuir 2006, 22, 10747-10753
[Non-patent Document 2] Yamaguchi, Journal of Power Sources, 2004, 138, 25-30

SUMMARY OF THE INVENTION

A problem to be solved by the present invention is to provide a surface modified material having a surface modified with a sulfonimide compound group having high oxygen permeation and high proton conductivity, a sulfonimide compound for surface modification for use in the production of such a surface modified material, and a fuel cell using such a surface modified material for a catalyst layer.

Moreover, another problem to be solved by the present invention is to provide a surface modified material in which outflow or leaving of the sulfonimide compound groups is unlikely to occur even when the equivalent weight of the sulfonimide compound groups is lowered and which is unlikely to lower the functions of a base material (for example, electric conductivity), a sulfonimide compound for surface modification for use in the production of such a surface modified material, and a fuel cell using such a surface modified material for a catalyst layer.

In order to solve the problems mentioned above, the surface modified material according to the present invention comprises the following configuration:
(1) The surface modified material comprises:
  a base material, and
  one or more kinds of sulfonimide compound groups bonded onto a surface of the base material via one or more linking group -A-Y'— (A is a direct bond, or an organic group. Y' is a bonding site with the base material.).
(2) The sulfonimide compound group comprises, in its molecular structure,
  one or more of the linking groups -A-Y'—, and
  two or more sulfonimide groups ($-SO_2NMSO_2-$. M is H or an alkali metal.).

The sulfonimide compound for surface modification according to the present invention comprises, in its molecular structure,
  one or more reactive end groups represented by formula (2), and
  two or more sulfonimide groups ($-SO_2NMSO_2-$. M is H or an alkali metal.).

$$-A-Y \quad (2)$$

where
  A is a direct bond or an organic group, and
  Y is a reactive functional group which is reactive with a base material for surface modification.

In addition, the fuel cell according to the present invention comprises using the surface modified material according to the present invention for a catalyst layer.

In the sulfonimide compound group, sulfonimide groups constituting the main chain function as proton conducting portions. Accordingly, the larger is the number of the sulfonimide groups contained in the molecular structure, the lower the EW of the surface modified material can be.

Moreover, in the surface modified material according to the present invention, the base material and the sulfonimide compound group are directly bonded, and therefore there is hardly a risk of outflow due to water even if the EW is lowered to the utmost limit. Moreover, a relatively large amount of sulfonimide groups can be introduced onto the surface of the base material via a relatively small amount of linking groups, therefore there is hardly a risk of leaving of the sulfonimide compound groups or lowering functions of the base material due to the lowered EW.

In addition, since the sulfonimide compound groups are bonded onto the surface of the base material via a relatively small amount of linking groups, oxygen permeation (diffusion, dissolution) is unlikely to be inhibited compared with the case where the surface of the base material is coated with electrolytic polymer. Accordingly, when such a surface modified material is applied to a catalyst layer of a fuel cell, its power generation performance is improved.

DESCRIPTION OF THE PREFERRED EMBODIMENT

One embodiment of the present invention will be described in detail below.
[1. Surface Modified Material]
The surface modified material according to the present invention comprises:
  a base material, and
  one or more kinds of sulfonimide compound groups bonded onto a surface of the base material via one or more linking groups -A-Y'— (A is a direct bond or an organic group. Y' is a bonding site with the base material.).
[1.1. Base Material]
The base material is for supporting sulfonimide compound groups. The base material may be any material as long as it has a surface which is reactive with a -A-Y group described later. The shape of the base material is not particularly limited, and may be any of particles, foils, fibers, plates and bars, among others.
There are specific examples of the base material such as:
(1) carbon having a graphite structure such as carbon nanotube (CNT), graphite, graphene, fullerene, carbon fiber and composites of these, (2) a metal cluster-supported carbon in which metal clusters that contain one or more kinds of metal elements (for example, noble metal elements such as Pt, Pd, transition metal elements, etc.) and have a diameter of 1 to several tens of nanometers are supported onto the surface of carbon,
(3) a metal material such as iron, copper, nickel, zinc and gold,
(4) a semiconductor material such as polysilane, polygermane and gallium arsenide,
(5) an organic material such as polyaniline,
(6) polytetrafluoroethylene,
(7) carbon having an oxidized surface and a graphite structure, or metal cluster-supported oxidized carbon having a surface with metal clusters supported thereon,
(8) a compound having —Si(OH) on its surface (for example, silica),
(9) carbon, metal, or inorganic oxide covered with a silane coupling agent,
(10) carbon in which amine is introduced onto its surface (for the synthesis method, refer to, for example, Japanese patent application Laid-open No. 2008-19120, etc.), among others.

Among these, carbon or metal cluster-supported carbon is preferable as the base material. With use of carbon or metal cluster-supported carbon as the base material, a surface modified material having excellent electronic conductivity and catalytic activity in addition to high oxygen permeability and high proton conductivity can be obtained.

[1.2. Sulfonimide compound group]

[1.2.1. Definition]

The term "sulfonimide compound group" means a group which comprises, in its molecular structure, one or more linking groups -A-Y— and two or more sulfonimide groups (—$SO_2NMSO_2$—. M is H or an alkali metal.).

The term "linking group -A-Y'—" means a group for connecting the sulfonimide compound group with the base material.

A represents a direct bond or an organic group. The term "organic group" means a group which has a saturated bond or an unsaturated bond between carbons in its molecular structure and has a valence of 2 or larger. The type of organic groups constituting A is not particularly limited, and various groups can be used depending on the purpose.

There are specific examples of organic groups such as:
(1) a bivalent aromatic hydrocarbon group such as —$C_6H_4$—, —$C_6H_4$—$C_6H_4$—, —$C_6H_4$—O—$C_6H_4$—, —$C_6H_4$—$SO_2$—$O_6H_4$—, —$C_6H_4$—$SO_2$—$C_6H_4$—$(CH_2)_n$—$C_6H_4$—, $C_6H_4$—$(CH_2)_n$—,

[Chemical formula 1]

(2) a bivalent aliphatic hydrocarbon group such as —$(CH_2)_n$—, $(CH_2)_n$—O—$(CH_2)_m$—,
(3) a perfluoroalkylene group such as —$(CF_2)_n$—, among others.

Among these, a preferable organic group is —$C_6H_4$—. This is because it has the advantage that in the case where Y in the -A-Y group described later is a diazonium salt, when A is —$C_6H_4$—, the diazonium salt is stabilized. Moreover, since —$C_6H_4$— has a low molecular weight, using this as the organic group A can lower the EW of the surface modified material.

Y' represents a bonding site with the base material. In the case where the base material and the reactive functional group Y described later are allowed to react, Y completely leaves the group and bonds to the base material in some cases, while Y is bonded to the base material in a state that part of Y remains in other cases. That is, the bonding site Y' represents a direct bond, or a group which remains after reaction between the reactive functional group Y and the base material. Y' may be bonded to the base material via a covalent bond or a coordination bond. When Y' is a residual group of the reactive functional group Y, the type of Y' is not particularly limited, and may be various groups depending on the types and combination of Y and the base material.

There are specific examples of Y' such as a direct bond, an amide bond, an ether bond, a quaternary ammonium salt structure, an ester bond, a sulfone bond, —$SO_2NH$—, —Si(O—)$_3$—, —SH . . . ( . . . represents a coordination bond with S), and —CH(-A)-$CH_2$—, among others.

The number of sulfonimide groups contained in a sulfonimide compound group may be two or larger. In general, the larger is the number of sulfonimide groups contained in a sulfonimide compound group, the lower the EW of the surface modified material can be.

The number of the linking group -A-Y'— contained in the sulfonimide compound group is not particularly limited, and may be optimally selected depending on the purpose. When the sulfonimide compound group has two or more linking groups -A-Y'— the sulfonimide compound group may be bonded to the base material via all of the linking groups -A-Y'—, or may be bonded to the base material via some of the linking groups -A-Y'—.

In addition, a single type of sulfonimide compound group may be bonded to the surface of the base material, or two or more kinds of sulfonimide compound groups having different molecular structures may be bonded.

[1.2.2. Specific Example 1]

A first specific example of the sulfonimide compound group comprises a structure represented by formula (1.1) or formula (1.2).

(1.1)

(1.2)

where
n is an integer from 1 to 50,
A is a direct bond or an organic group,
Y' is a bonding site with the base material,
Rf is a perfluoroalkylene group having 1 to 10 carbon atoms; Rf may have a branched and/or an annular structure,
M is H or an alkali metal, and
R is OH, $NH_2$, or $NHSO_2R'$ (R' is a monovalent group having a saturated bond or an unsaturated bond between carbons in its molecular structure.).

n represents the number of repetition of perfluorosulfonimide groups ($RfSO_2NMSO_2$). A sulfonimide group in which a perfluoroalkylene group Rf is bonded to at least one end functions as a strong acid group. In order to obtain high acidity, the perfluoroalkylene groups Rf are preferably bonded to both ends of the sulfonimide group. Therefore, n is preferably 1 or larger. n is more preferably 5 or larger.

In general, the larger the n is, the lower the EW of the surface modified material. However, when n is excessively large, it is difficult to synthesize the sulfonimide compound at a high yield. Therefore, n is preferably 50 or smaller. n is more preferably 30 or smaller.

A represents a direct bond or an organic group. Moreover, Y' represents a bonding site with the base material. The details of A and Y' are as mentioned above, and their explanation is thus omitted.

Rf represents a perfluoroalkylene group. Rf may have a chain structure, or may have a branched and/or an annular structure.

Rf may have one or more carbon atoms. In general, the larger the number of carbon atoms in Rf, the higher the hydrophobicity, and therefore the easier to support onto a hydrophobic base material such as carbon. The number of carbon atoms in Rf is more preferably 2 or larger.

In contrast, when the number of carbon atoms in Rf is excessively larger, proton conductivity is lowered. Therefore, the number of carbon atoms in Rf is preferably 10 or smaller. The number of carbon atoms in Rf is more preferably 5 or smaller.

M represents a cation which ionically bonds with $N^-$ in the sulfonimide group ($-SO_2N^-(M^+)SO_2-$) M may be either H or an alkali metal.

In formula (1.2), R represents OH, $NH_2$; or $NHSO_2R'$. R' represents a monovalent group which has a saturated bond or an unsaturated bond between carbons in its molecular structure. There are specific examples of R' such as an aromatic group, and a perfluoroalkyl group Rf', among others.

There are specific examples of the aromatic group such as $-C_6H_5$, $-C_6H_4-C_6H_5$, $-C_6H_4-O-C_6H_5$, $-C_6H_4-SO_2-C_6H_5$, $-C_6H_4-SO_2-(CH_2)_n-(C_6H_5)$, $-(CH_2)_n-C_6H_5$,

[Chemical formula 2]

among others.

The perfluoroalkyl group Rf' may have a chain structure, or may have a branched and/or an annular structure.

Rf' may have one or more carbon atoms. In general, the larger the number of carbon atoms in Rf', the higher the hydrophobicity, and therefore the easier to support onto a hydrophobic base material such as carbon. The number of carbon atoms in Rf' is more preferably 2 or larger.

In contrast, when the number of carbon atoms in Rf' is excessively large, proton conductivity is lowered. Therefore, the number of carbon atoms in Rf' is preferably 10 or smaller. The number of carbon atoms in Rf' is more preferably 5 or smaller.

[1.2.3. Specific Example 2]

There are such other examples of the sulfonimide compound group that have $-[RfSO_2NMSO_2]_n$-A-Y'— bonded at an end of a side chain of a fluorinated electrolytic polymer such as Nafion (registered trademark).

[1.3. Loading Amount of Sulfonimide Compound Groups]

The loading amount of sulfonimide compound groups on the surface of the base material is not particularly limited, and may be optimally selected depending on the purpose. In general, the larger is the loading amount of the sulfonimide compound groups, the lower the EW of the surface modified material can be.

[2. Sulfonimide Compound for Surface Modification]
[2.1. Definition]

The sulfonimide compound for surface modification according to the present invention comprises, in its molecular structure, one or more reactive end groups represented by formula (2), and two or more sulfonimide groups ($-SO_2NMSO_2-$. M is H or an alkali metal.).

$$-A-Y \quad (2)$$

where

A is a direct bond or an organic group, and

Y is a reactive functional group which is reactive with a base material for surface modification.

In formula (2), A represents a direct bond or an organic group. The details of A are as mentioned above, and their explanation is thus omitted.

Y represents a reactive functional group which is reactive with the base material for surface modification. The type of Y is not particularly limited as long as it is reactive with the base material.

There are specific examples of Y such as $-NH_2$, a diazonium salt represented by $-N^+\equiv NX^-$ (X is a counteranion), epoxy, methacryl, carboxylic acid, carboxylic acid halide, sulfonamide, $-Si(OR)_3$, $-(CH_2)Hal$ (Hal=Cl, Sr, I), $-OH$, $-SH$, and $-CH=CH_2$, among others.

Y may be reactive directly with the base material, or reactive with the base material after Y has been converted into an appropriate functional group. When conversion of the functional group of Y is necessary, the conversion may be performed before being brought into contact with the base material, or may be performed while in contact with the base material.

For example, when Y is a diazonium salt, Y normally acts as a reaction starting point when Y is allowed to react with the base material.

In contrast, when Y is $NH_2$, the $-NH_2$ group becomes a reaction starting point in some cases, while it does not in other cases. For example, when the surface of the base material comprises an oxide such as $C(=O)OH$ and $C(=O)Cl$, the $-NH_2$ groups and the base material can be directly allowed to react. In contrast, when the reactivity between the surface of the base material and the $-NH_2$ groups is low, allowing reaction between a compound having a $-NH_2$ group at its end and a nitrite such as sodium nitrite easily allows conversion of the $-NH_2$ group into a diazonium salt.

Moreover, in the case where Y is SH, when the base material is gold (regardless of the form, such as particles, bulk, etc.) mixing these in an organic solvent allows reaction between them.

[2.2. Specific Example 1]

A first specific example of the sulfonimide compound for surface modification comprises a structure represented by formula (2.1) or formula (2.2).

$$-Y'-A-SO_2NMSO_2-[RfSO_2NMSO_2]_n-A-Y'- \quad (2.1)$$

$$-Y'-A-SO_2NMSO_2-[RfSO_2NMSO_2]_n-RfSO_2R- \quad (2.2)$$

where n is an integer from 1 to 50,

A is a direct bond or an organic group,

Y is a reactive functional group which is reactive with a base material for surface modification, Rf is a perfluoroalkylene group having 1 to 10 carbon atoms; Rf may have a branched and/or an annular structure, M is H or an alkali metal, and R is OH, NH$_2$, or NHSO$_2$R' (R' is a monovalent group having a saturated bond or an unsaturated bond between carbons in its molecular structure.).

In formula (2.1) and formula (2.2), the details of n, A, Y, Rf, M and R are as mentioned above, and their explanation is thus omitted.

[2.3. Specific Example 2]

There are such other examples of the sulfonimide compound that have a —[RfSO$_2$NMSO$_2$]$_n$-A-Y group bonded at an end of a side chain of a fluorinated electrolytic polymer such as Nafion (registered trademark).

[3. Method for Producing Sulfonimide Compound for Surface Modification]

The sulfonimide compound for surface modification can be produced by various methods.

For example, a sulfonimide compound represented by formula (2.1) or formula (2.2) can be synthesized by the following procedure.

That is, first, according to formula (a), perfluoro disulfonamide (CmA) in which the number of carbon atoms is m and perfluoro disulfonyl fluoride (CmF) in which the number of carbon atoms is m are allowed to react in the coexistence with a base, thereby obtaining polyperfluoro sulfonimide (PCmFSI) In this case, the number m of carbon atoms of CmA and the number m of carbon atoms of CmF are not necessarily the same.

(a)

Second, by allowing reaction between one or both of —SO$_2$NH$_2$ groups located at the ends thereof and various organic compounds, -A-Y groups are introduced into the ends of PCmFSI.

For example, the sulfonimide compound in which the -A-Y group is —C$_6$H$_4$—NH$_2$ can be produced by:
(1) allowing reaction between PCmFSI and 4-acetamide benzene sulfonyl chloride to bond a —C$_6$H$_4$—NHC(═O)CH$_3$ group at the end of PCmFSI, and
(2) further adding a hydrochloric acid/ethanol mixed solution and heating the mixed solution to convert acetamide groups to amide groups.

In this case, if the reaction proceeds ideally, only the sulfonimide compound of formula (2.1) is produced. Depending on the reaction conditions, a mixture of the sulfonimide compound of formula (2.1) and the sulfonimide compound of formula (2.2) may be obtained.

Moreover, for example, a sulfonimide compound in which a —C$_6$H$_4$—NH$_2$ group is bonded at the end of a fluorinated electrolytic polymer such as Nafion (registered trademark) can be synthesized by:
(1) sulfonimidating its ends by allowing a fluorinated electrolytic polymer having sulfonamidated ends to react with CmF and CmA in the coexistence with a base, and
(2) introducing a —C$_6$H$_4$—NH$_2$ group into the end according to the procedure similar to that described above.

Likewise, other sulfonimide compounds can be produced by using a method similar to the above-mentioned method.

[4. Method for Producing Surface Modified Material]

The surface modified material according to the present invention can be produced by allowing reaction between the base material and the sulfonimide compound.

For example, a surface modified material in which the -A-Y group of the sulfonimide compound is the -A-NH$_2$ group and the base material is carbon or metal cluster-supported carbon can be produced by:

(1) treating the sulfonimide compound with sulfuric acid in advance to promote the N$_2$ elimination reaction of the diazonium salt (to make the counteranion X$^-$ of the diazonium salt HSO$_4^-$),
(2) treating the sulfonimide compound treated with sulfuric acid with nitrite to convert the -A-NH$_2$ group to -A-N$^+$N$^+$═NX$^-$, and
(3) allowing reaction between -A-N$^+$═N and the surface of the base material.

In this case, the temperature for adding nitrite is preferably 0° C. to 60° C., and is more preferably 0° C. to room temperature. Moreover, in order to support the sulfonimide groups uniformly onto the surface of a base material, it is preferable that the temperature is gradually raised with stirring.

Moreover, for example, a surface modified material in which the -A-Y group of the sulfonimide compound is the -A-NH$_2$ group and the base material is a metal material such as iron can be produced by:
(1) according to a procedure similar to those of above-mentioned
(1) and (2), converting the -A-NH$_2$ group to -AN$^+$═NX$^-$, and
(2) after immersing the base material in a sulfuric acid solution of the sulfonimide compound, and sonicating the base material with acetone to remove unnecessary components.

Moreover, for example, a surface modified material in which the -A-Y group of the sulfonimide compound is the -A-NH$_2$ group and the base material is polysilane or polygermane can be produced by:
(1) allowing reaction between the sulfonimide compound and tetrafluoroboric acid and then drying a reaction product, and
(2) allowing reaction between polysilane and the like which are surface-treated in a glove box in an inert atmosphere and a dry matter obtained in (1), in acetonitrile in the presence of isoamyl nitrite.

Moreover, for example, a surface modified material in which the -A-Y group of the sulfonimide compound is -A-NH$_2$ group and the base material is surface oxidized carbon can be produced by allowing reaction between the sulfonimide compound and the surface of the base material in the existence of a base.

Moreover, for example, a surface modified material in which the -A-Y group of the sulfonimide compound is a -A-SH group and the base material is Au can be produced by mixing the sulfonimide compound and Au in a solution.

Moreover, for example, a surface modified material in which the -A-Y group of the sulfonimide compound is a -A-Si(OR)$_3$ group and the base material is silica can be produced by mixing the sulfonimide compound and the base material in a solution and then heating the mixture.

Moreover, for example, a surface modified material in which the -A-Y group of the sulfonimide compound is a -A-OH group and the base material is carbon surface-treated with an epoxylated silane coupling agent can be produced by mixing the sulfonimide compound and the base material in a solution and then heating the mixture.

Likewise, other surface modified materials can be produced by using a method similar to the above-mentioned method.

[4. Fuel Cell]

The fuel cell according to the present invention comprises using the surface modified material according to the present invention for a catalyst layer. The catalyst layer, in general, comprises a complex of a catalyst (or a catalyst supported on carrier) and catalyst layer ionomers. When the surface modified material according to the present invention is used for the catalyst layer, the catalyst layer may contain the surface modified material according to the present invention and without containing catalyst layer ionomers, or may contain both.

When the surface modified material according to the present invention is used for the catalyst layer, carbon or metal cluster-supported carbon is preferable as the base material. When the base material is metal cluster-supported carbon, it is considered that the sulfonimide compound groups hardly cover metal cluster particles. Accordingly, the catalyst layer using the surface modified material according to the present invention has higher oxygen permeation than known catalyst layers produced by mixing electrolytic polymers. That is, the surface modified material according to the present invention can be used for both an anode-side catalyst layer and a cathode-side catalyst layer, but especially favorable for the cathode-side catalyst layer.

[5. Functions of Surface Modified Material, Sulfonimide Compound for Surface Modification, and Fuel Cell]

In the sulfonimide compound group, sulfonimide groups constituting the main chain function as proton conducting portions. Accordingly, the larger is the number of the sulfonimide groups contained in the molecular structure, the lower the EW of the surface modified material can be.

Moreover, in the surface modified material according to the present invention, the base material and the sulfonimide compound group are directly bonded, and therefore there is hardly a risk of outflow due to water even if the EW is lowered to the utmost limit. Moreover, a relatively large amount of sulfonimide groups can be introduced onto the surface of the base material via a relatively small amount of linking groups, therefore there is hardly a risk of leaving of the sulfonimide compound groups or lowering functions of the base material due to the lowered EW.

In addition, since the sulfonimide compound groups are bonded onto the surface of the base material via a relatively small amount of linking groups, oxygen permeation (diffusion, dissolution) is unlikely to be inhibited compared with the case where the surface of the base material is coated with electrolytic polymer. Accordingly, when such a surface modified material is applied to a catalyst layer of a fuel cell, its power generation performance is improved.

EXAMPLES

Example 1

Polyperfluoropropyl sulfonimide (PC3FSI) having sulfonamide at both ends and 4-acetamide benzenesulfonyl chloride were mixed in acetonitrile. N,N-diisopropyl ethyl amine (DIPEA) was added to the mixture. The mixture was stirred at 80° C. for two days. After the completion of the reaction, a hydrochloric acid/ethanol mixed solution was added to the reaction mixture, which was then heated at 80° C. for two hours. Thereafter, an aqueous solution of NaOH was added to the mixture to make it alkaline, and an organic layer was extracted with acetonitrile. The obtained organic layer was dried, thereby obtaining a sulfonimide compound with both ends protected by aniline. Formula (b) below shows its synthesis reaction formula.

[Chemical formula 3]

Example 2

1. Preparation of Surface Modified Material

The sulfonimide compound obtained in Example 1 and a Pt-supported carbon material (carbon type: ketjen) were dispersed in a water-alcohol mixed solvent, and the mixture was then stirred with the addition of sulfuric acid. Thereafter, sodium nitrite was added to the mixture. The mixture was then stirred and heated gradually from room temperature to 60° C. and retained for one hour. Thereafter, the mixture was allowed to cool down to room temperature, and was repeatedly subjected to pressure filtration to clean a solid portion.

2. Evaluation Method and Results

Figure 1:
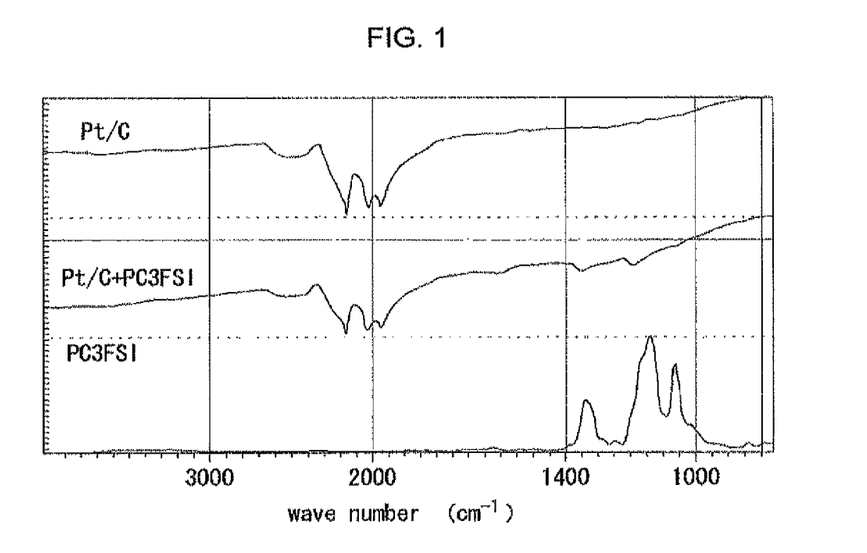
FIG. 1 is an FT-IR spectrum of the surface modified material obtained in Example 2, and a raw material of the same, Pt/C and PC3FSI.
Figure 2:
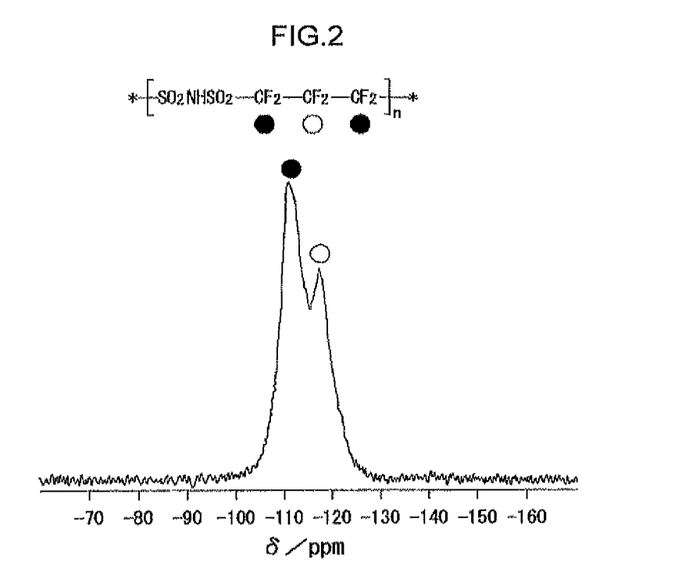
FIG. 2 is a solid-state $^{19}F$ NMR spectrum of the surface modified material obtained in Example 2.

After the solid portion was dried, it was measured by FT-IR and solid-state $^{19}$F NMR. FIG. 1 shows the FT-IR spectrum of the surface modified material obtained in Example 2. In FIG. 1, "PC3FSI" represents the sulfonimide compound before its both ends were protected by aniline. Moreover, FIG. 2 shows the solid-state $^{19}$F NMR spectrum of the surface modified material obtained in Example 2.

As shown in FIG. 1, clear three peaks are found in the range from 1000 to 1400 cm$^{-1}$ with PC3FSI, while no such peak exists with Pt/C. In contrast, a weak peak was found in a position similar to that of PC3FSI with the surface modified material obtained in Example 2. In addition, as shown in FIG. 2, a peak (black circle) corresponding to C at both ends of —$CF_2$—$CF_2$—$CF_2$— and a peak (white circle) corresponding to the central C were found with the surface modified material obtained in Example 2. It can be seen from FIGS. 1 and 2 that a surface modified material in which sulfonimide compound groups were supported on the surface of carbon was obtained.

Example 3

The surface modified material obtained in Example 2 was dispersed in a solvent mixture of water and ethanol, thereby obtaining a catalyst ink. This catalyst ink was applied onto the surfaces of an electrolyte membrane with a spray. In addition, this was hot-pressed at 130° C. Furthermore, both sides of the electrolyte membrane were put between diffusion layers, to obtain a membrane electrode assembly (MEA). A fuel cell power generation test was performed using the obtained MEA. It was confirmed from the results that power was generated.

Example 4

The sulfonimide compound obtained in Example 1 was dissolved in a solvent mixture of water and alcohol. Sulfuric acid was added to the mixture, and then sodium nitrite was added thereto at 0° C. This solution was applied to CNT which was vertically oriented on a substrate, and was heated.

It was confirmed that the sulfonimide compound was bonded and grafted onto the surface of CNT, and that protons conducted.

Example 5

1. Preparation of Surface Modified Material

The sulfonimide compound obtained in Example 1 was dissolved in 10 mL of ethanol. Sulfuric acid (0.45 g) was added to the solution, and a precipitate in the mixture was filtered. Nitrosyl tetrafluoroborate (NOBF4) (0.12 g) was added to this filtrate at room temperature, and the mixture was stirred overnight.

The solvent was removed from the mixture. The mixture was then vacuum-dried, obtaining a diazonium compound. Pt-supported carbon (carbon type: Vulcan) was admixed to this compound. A water-ethanol (5 mL:5 mL) mixture was added to this admixture, and the resulting mixture was stirred. The mixture was then gradually heated from room temperature to 60° C., and was retained for one hour. The mixture was then cooled to room temperature, and was repeatedly subjected to pressure filtration to wash a solid portion (surface modified material).

2. Evaluation Method and Results

Figure 3:
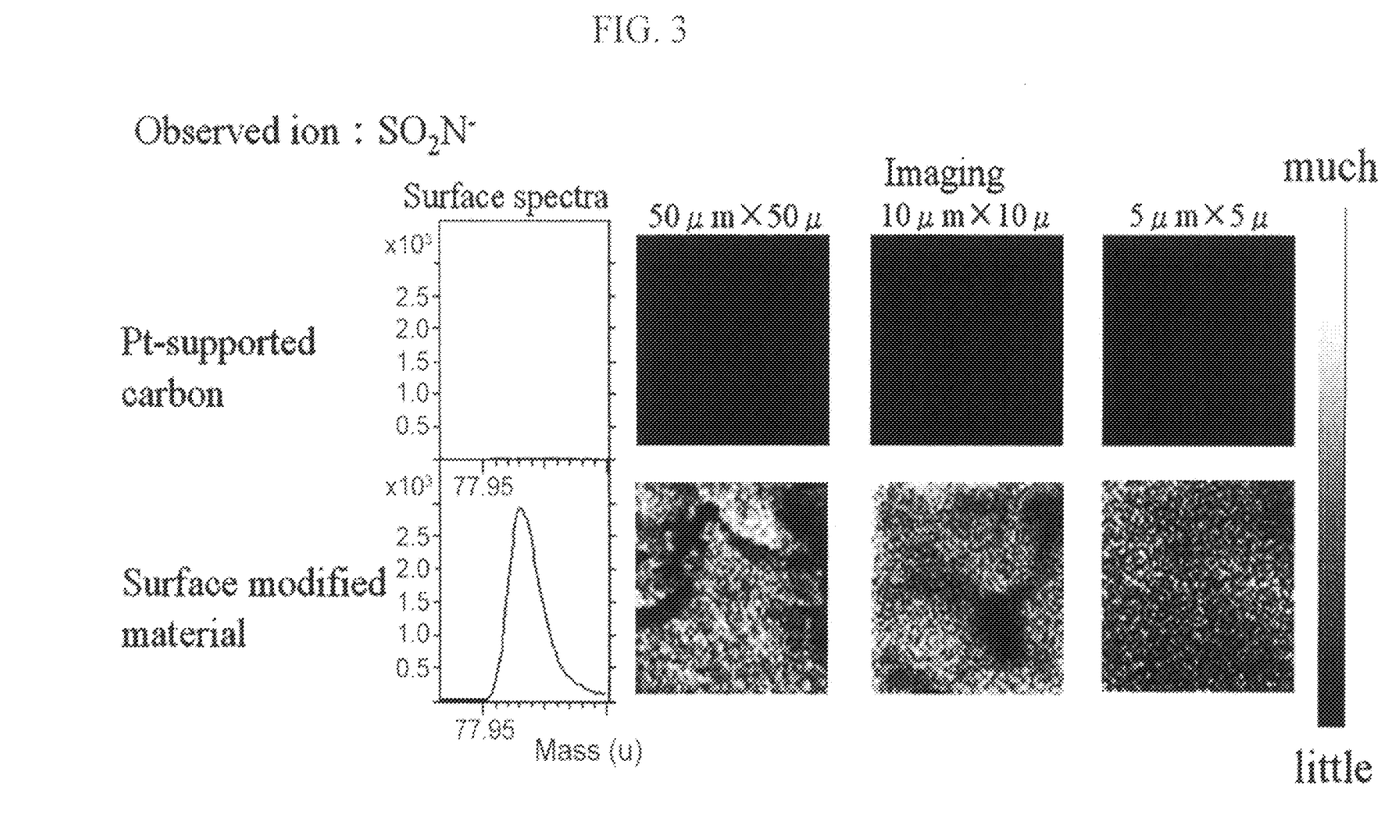
FIG. 3 shows ion spectra of the surfaces of the surface modified material obtained in Example 5.

The solid portion was measured by FT-IR and solid-state $^{19}$FNMR. It was confirmed from the results that ionomers were supported on the surface of the Pt-supported carbon as in Example 2. In addition, an ion spectrum on the surface of the modified material was observed by TOF-SIMS (FIG. 3). It can be seen that $SO_2N^-$ ions are uniformly distributed on the surface of the carbon after the modification of the surface.

Example 6

The same reactions as that in Example 5 were performed using surface modified materials with different numbers of repetition (n) of sulfonimide. The amounts of sulfonimide contained in the obtained surface modified materials were quantified by solid-state $^{19}$F NMR spectroscopy. The results are shown in Table 1.

TABLE 1

|   | n    | Amounts of sulfonimide (wt. %) |
|---|------|--------------------------------|
| 1 | 13.2 | 2.2                            |
| 2 | 38.6 | 1.7                            |
| 3 | 8.4  | 5.6                            |

Example 7

1. Preparation of MEA

A membrane-electrode assembly (MEA) was prepared according to the following procedure.

First, the surface modified material obtained in Example 5 was dispersed in a solvent mixture of ethanol and water. The resulting solution was coated onto a polytetrafluoroethylene sheet and dried. The resulting sheet was used as a transfer catalyst layer for cathode. No surface modified material was used for the anode, and a transfer catalyst layer prepared by a known method was used.

The transfer catalyst layer for cathode and transfer catalyst layer for anode were bonded by hot pressing onto one side of an electrolyte membrane (NR211, manufactured by DuPont) and the other side thereof, respectively, giving an MEA (a) for evaluation. The electrode area was 1 cm$^2$.

As an MEA for comparison, an MEA (b) having a catalyst layer for cathode bonded thereto was prepared. The layer used Pt-supported carbon (Vulcan) and a dispersion (DE2020, DuPont) of Nafion (registered trademark).

2. Evaluation of Endurance of MEA

First of all, the following conditioning was performed at a cell temperature of 80° C.

First, hydrogen (279 sccm) and nitrogen (680 sccm), which were humidified to a relative humidity (RH) of 100%, were introduced into the anode and cathode, respectively. 30 cycles of sweeping were performed with the potential of the cathode relative to the anode between 0.05 V and 1.20 V and at a sweeping speed of 100 mV/s. Air (680 sccm), in place of nitrogen, humidified to an RH of 100% was then introduced into the cathode, and the operation was continued for 30 minutes at 2.0 A/cm$^2$.

RF values ECSA/the apparent area of the electrode) were determined in the endurance evaluation by performing the following procedure.

Hydrogen (279 sccm) and nitrogen (680 sccm), which were humidified to a relative humidity (RH) of 100%, were introduced into the anode and cathode, respectively, and 500 cycles of sweeping were performed between 0.1 V and 1.0 V at a sweeping speed of 50 mV/s. RF values ("pre-endurance") were determined with 210 μC/cm$^2$ Pt, electrode area 1 cm$^2$, and by use of the quantity of electricity of hydrogen desorption in the 30th cycle.

Second, 500 cycles of sweeping were performed between 0.1 V and 1.0 V at a sweeping speed of 50 mV/s using the same gas to determine RF values ("during-endurance").

Finally, 500 cycles of sweeping were performed between 0.1 V and 1.2 V at a sweeping speed of 50 mV/s using the same gas to determine RF values ("post-endurance").

Figure 4:
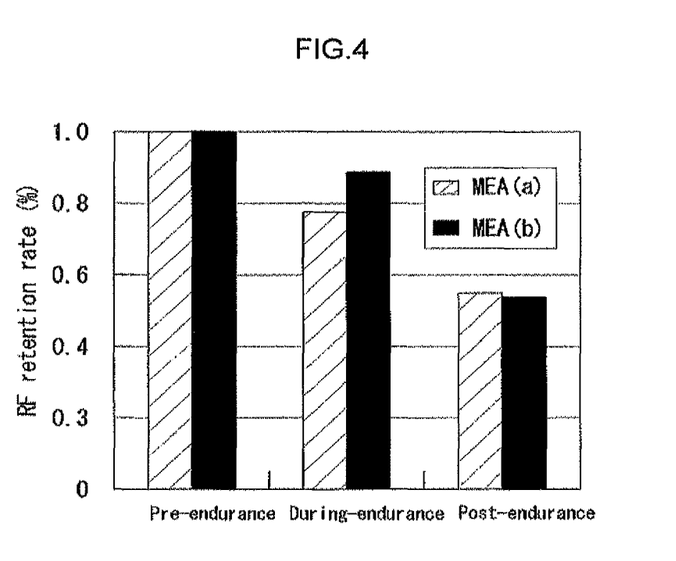
FIG. 4 shows RF retention rate of MEA (a) using a catalyst layer for cathode containing the surface modified material according to the present invention and MEA (b) using a known catalyst layer for cathode.

The pre-endurance, during-endurance and post-endurance RF values for the MEA (a) and MEA (b) were compared to calculate the retention rate of the RF values relative to the pre-endurance values. They showed no significant difference (FIG. 4). It was determined from this result that the durability of the surface modified material was almost the same as that of the MEA having Nafion (registered trademark) coated thereto.

The embodiments of the present invention have been described above in detail, but the present invention is not limited to the above-described embodiments in any way, and various modifications are possible as long as they do not deviate from the scope of the present invention.

The surface modified material according to the present invention can be used for, among others:

(1) catalyst layers for MEA for use in various electrochemical devices such as solid polymer fuel cells, water electrolysis apparatuses, halogenated hydroacid electrolysis apparatuses, salt electrolysis apparatuses, oxygen and/or hydrogen concentrating apparatuses, humidity sensors, gas sensors, and the like, and (2) cation exchange resins.

What is claimed is:

1. A surface modified material comprising:
a base material selected from the group consisting of a carbon having a graphite structure; a metal cluster-supported carbon in which metal clusters that contain one or more kinds of metal elements are supported on a surface of the carbon; a metal material; a semiconductor material; a carbon having an oxidized surface and a graphite structure, or metal cluster-supported oxidized carbon having a surface with metal clusters supported thereon; a compound having —Si(OH) on a surface thereof; a carbon, metal, or inorganic oxide covered with a silane coupling agent; and a carbon in which an amine is introduced onto a surface thereof; and one or more kinds of sulfonimide compound groups bonded onto a surface of the base material via one or more linking groups -A-Y'—, wherein:

A is an organic group selected from the group consisting of —(CH$_2$)$_n$—, —(CH$_2$)$_n$—O—(CH$_2$)$_m$—, —C$_6$H$_4$—, —C$_6$H$_4$—C$_6$H$_4$—, —C$_6$H$_4$—O—C$_6$H$_4$—, —C$_6$H$_4$—SO$_2$—C$_6$H$_4$—, —C$_6$H$_4$—SO$_2$—C$_6$H$_4$—(CH$_2$)$_n$—C$_6$H$_4$—, —C$_6$H$_4$—(CH$_2$)$_n$—, Y' is a bonding site with the base material and is selected from the group consisting of a direct bond, an amide bond, an ether bond, a quaternary ammonium salt structure, an ester bond, a sulfone bond, —SO$_2$NH—, —Si(O—)$_3$—, and —SH—, where — represents a coordination bond with S; and the sulfonimide compound group comprises, in its molecular structure, one or more of the linking groups -A-Y'—, and two or more —SO$_2$NMSO$_2$— groups, where M is H or an alkali metal.

2. The surface modified material according to claim 1, wherein the sulfonimide compound group has a structure represented by formula (1.1) or formula (1.2):

—Y'-A-SO$_2$NMSO$_2$-[RfSO$_2$NMSO$_2$]$_n$-A-Y'-    (1.1)

—Y'-A-SO$_2$NMSO$_2$-[RfSO$_2$NMSO$_2$]$_n$—RfSO$_2$R    (1.2), where
n is an integer from 1 to 50,
Rf is a perfluoroalkylene group having 1 to 10 carbon atoms,
Rf has a branched and/or an annular structure,
R is OH, NH$_2$, or NHSO$_2$R', and
R' is a monovalent group having a saturated bond or an unsaturated bond between carbons in its molecular structure.

3. The surface modified material according to claim 1, wherein the base material is a carbon having a graphite structure or a metal cluster-supported carbon in which metal clusters that contain one or more kinds of metal elements are supported on a surface of the carbon.

4. A fuel cell comprising a catalyst layer, wherein the catalyst layer comprises the surface modified material according to claim 1.

5. The surface modified material according to claim 1, wherein the base material is selected from the group consisting of a carbon having a graphite structure; a metal cluster-supported carbon in which metal clusters that contain one or more kinds of metal elements are supported on a surface of the carbon; a metal material; a semiconductor material; a carbon having an oxidized surface and a graphite structure, or metal cluster-supported oxidized carbon having a surface with metal clusters supported thereon; and a carbon, metal, or inorganic oxide covered with a silane coupling agent.

6. The surface modified material according to claim 1, wherein the sulfonimide compound group comprises, in its molecular structure, six or more —SO$_2$NMSO$_2$-groups.

* * * * *